(12) United States Patent
Chakravarty et al.

(10) Patent No.: US 9,301,890 B2
(45) Date of Patent: Apr. 5, 2016

(54) ABSORBENT ARTICLES IN A UNITARY PACKAGE

(71) Applicant: Kimberly-Clark Worldwide, Inc., Neenah, WI (US)

(72) Inventors: Jayant Chakravarty, Woodbury, MN (US); David Louis Zenker, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 66 days.

(21) Appl. No.: 13/621,911

(22) Filed: Sep. 18, 2012

(65) Prior Publication Data

US 2013/0014475 A1    Jan. 17, 2013

Related U.S. Application Data

(62) Division of application No. 10/952,014, filed on Sep. 28, 2004, now abandoned.

(51) Int. Cl.
| | | |
|---|---|---|
| *A61F 13/15* | (2006.01) | |
| *A61F 13/20* | (2006.01) | |
| *A61F 13/84* | (2006.01) | |
| *A61F 13/551* | (2006.01) | |
| *A61F 15/00* | (2006.01) | |

(52) U.S. Cl.
CPC ........... *A61F 13/84* (2013.01); *A61F 13/15617* (2013.01); *A61F 13/15747* (2013.01); *A61F 13/15804* (2013.01); *A61F 13/55115* (2013.01); *A61F 15/001* (2013.01); *A61F 2013/8497* (2013.01)

(58) Field of Classification Search
CPC .................................. A61F 13/20; A61F 13/15
USPC ....................... 604/385.01, 317, 358, 385.02; 206/438–441, 459.5; 493/256
See application file for complete search history.

(56) References Cited

U.S. PATENT DOCUMENTS

| | | | |
|---|---|---|---|
| 3,635,567 A * | 1/1972 | Richardson, Jr. ............. 401/132 |
| 4,666,647 A | 5/1987 | Enloe et al. |
| 4,761,258 A | 8/1988 | Enloe |
| 5,149,335 A | 9/1992 | Kellenberger et al. |
| 5,163,558 A | 11/1992 | Palumbo et al. |
| 5,235,515 A * | 8/1993 | Ungpiyakul et al. ......... 700/125 |
| 5,286,543 A * | 2/1994 | Ungpiyakul et al. ...... 428/32.24 |
| 5,458,062 A * | 10/1995 | Goldberg et al. ............. 101/485 |
| 5,725,382 A | 3/1998 | Walter et al. |
| 5,818,719 A * | 10/1998 | Brandon et al. ............... 700/125 |
| 5,858,515 A | 1/1999 | Stokes et al. |

(Continued)

FOREIGN PATENT DOCUMENTS

| | | |
|---|---|---|
| WO | 0230347 A1 | 4/2002 |
| WO | 02094678 A1 | 11/2002 |
| WO | 03022196 A2 | 3/2003 |

*Primary Examiner* — Michele M Kidwell
(74) *Attorney, Agent, or Firm* — Armstrong Teasdale LLP (57) ABSTRACT

A method of forming disposable absorbent articles includes forming at least two different types of absorbent articles on a single product line. Each type of absorbent article has an absorbent structure that differs from the absorbent structure of at least one other absorbent article type on the product line. The method further includes creating a visual distinction between the different types of absorbent articles and packaging the different types of absorbent articles in a single package.

7 Claims, 8 Drawing Sheets

(56) References Cited

U.S. PATENT DOCUMENTS

| | | | |
|---|---|---|---|
| 5,865,322 A | 2/1999 | Miller | |
| 5,897,542 A | 4/1999 | Lash et al. | |
| 5,928,452 A * | 7/1999 | McFall et al. | 156/269 |
| 5,980,087 A * | 11/1999 | Brandon et al. | 700/125 |
| 6,045,544 A * | 4/2000 | Hershberger et al. | 604/385.01 |
| 6,183,587 B1 * | 2/2001 | McFall et al. | 156/201 |
| 6,195,800 B1 * | 3/2001 | Gilmer et al. | 2/67 |
| 6,220,999 B1 * | 4/2001 | Kugler et al. | 493/256 |
| 6,222,091 B1 | 4/2001 | Beihoffer et al. | |
| 6,316,388 B1 * | 11/2001 | Schutze et al. | 504/215 |
| 6,454,095 B1 | 9/2002 | Brisebois et al. | |
| 6,558,499 B1 * | 5/2003 | Pargass et al. | 156/250 |
| 6,601,705 B2 | 8/2003 | Molina et al. | |
| 6,685,020 B2 | 2/2004 | Briseboi et al. | |
| 6,689,934 B2 | 2/2004 | Dodge, II et al. | |
| 7,172,667 B2 * | 2/2007 | Vergona | 156/64 |
| 7,179,851 B2 | 2/2007 | Qin et al. | |
| 7,185,761 B2 * | 3/2007 | Molina et al. | 206/494 |
| 7,696,401 B2 | 4/2010 | Qin et al. | |
| 2002/0152001 A1 * | 10/2002 | Knipp et al. | 700/100 |
| 2003/0139715 A1 | 7/2003 | Dodge, II et al. | |
| 2003/0139721 A1 * | 7/2003 | Melius et al. | 604/385.01 |
| 2004/0102748 A1 | 5/2004 | Hirotsu | |
| 2004/0143231 A1 * | 7/2004 | Nair et al. | 604/385.01 |
| 2005/0127791 A1 * | 6/2005 | Ikeda et al. | 310/328 |
| 2006/0069372 A1 * | 3/2006 | Chakravarty et al. | 604/385.02 |
| 2006/0135927 A1 * | 6/2006 | Zander et al. | 604/385.02 |
| 2006/0224133 A1 * | 10/2006 | Gannon et al. | 604/385.03 |

* cited by examiner

ABSORBENT ARTICLES IN A UNITARY PACKAGE

CROSS-REFERENCE TO RELATED APPLICATION

This application is a divisional application of U.S. patent application Ser. No. 10/952,014 entitled Absorbent Articles in a Unitary Package, filed Sep. 28, 2004, which is fully incorporated herein by reference.

BACKGROUND OF THE INVENTION

This invention is directed to multiple types of absorbent articles provided in a single package, as well as a method of providing such a package, and a method of forming various types of absorbent articles.

Absorbent articles, such as diapers, are often over-designed in order to provide a single type of absorbent article that can accommodate a wide range of users in a wide range of usage conditions. More particularly, absorbent structures within absorbent articles are often designed to have a considerably high absorbent capacity and/or product design that is sufficient for both normal and extreme usage conditions. However, the use of excess absorbent material and/or more expensive absorbent material in garments that are used under normal usage conditions results in unnecessarily high material costs.

Specially-designed products for specific usage conditions, such as daytime wear or more absorbent overnight wear, are available. However, in order for a consumer to use the appropriate articles at the appropriate time, the consumer must purchase a package of each type of absorbent article. The multiplicity of packages takes up storage space and may be cumbersome to contend with in terms of finding the appropriate package at the appropriate time. Additionally, each product type is typically produced on a separate product line. This multiplicity of product lines also takes up space, as well as requiring additional equipment as well as supervision.

There is thus a need or desire for a package of absorbent articles that can provide suitable articles for various usage conditions without requiring excess storage space. There is a further need or desire for a method of making absorbent articles that can produce multiple types of absorbent articles simultaneously on a single product line.

SUMMARY OF THE INVENTION

In response to the discussed difficulties and problems encountered in the prior art, a new package of absorbent articles, as well as methods of forming such absorbent articles, has been discovered. This single package contains different types of absorbent articles and therefore obviates the need to buy multiple packages each containing a different type of absorbent article. Additionally, the method of forming multiple types of absorbent articles on a single product line reduces the amount of space and equipment normally required to maintain multiple product lines. The principles of the invention may be applied to any of a number of disposable absorbent article applications, such as diapers, diaper pants, training pants, swimwear, adult incontinence products, feminine care products, and the like.

In accordance with the invention, a single package of disposable absorbent articles may include at least two different types of disposable absorbent articles each having an absorbent structure. The absorbent structures are specific to each absorbent article type, and thus the absorbent structure of each type of absorbent article is different than the absorbent structure of the other type(s) of absorbent articles. Also, each type of absorbent article has an appearance that is visibly distinguished from the other type(s) of absorbent articles.

The absorbent structures may differ among the absorbent article types in one or more ways. For example, one type of absorbent article may have a greater absorbent capacity than another type of absorbent article. Alternatively, the absorbent structure may be narrower in a crotch region width, and/or narrower in a front region width, and/or narrower in a back region width in one absorbent article type than in another absorbent article type. The absorbent structure may also vary in length among the absorbent article types. As another example, the absorbent structure may be zoned differently in the different types of absorbent articles, with either no zoning present in one type and/or different zoning in front/back or front/crotch/back regions among the absorbent article types. Furthermore, the absorbent structure may be bonded or embossed differently among the absorbent article types, and/or not bonded or embossed at all in one of the absorbent article types. In certain embodiments, different types of superabsorbent material may be used among the different types of absorbent articles. As yet another example of possible differentiating features among the types of absorbent articles, a specific type of surge layer may be present in the absorbent structure of one type and the absorbent structure of another type may have either no surge layer or a different type of surge layer.

The frequency of the different types of absorbent articles within a single package may be any suitable frequency. For example, in a package containing at least two different types of absorbent articles, the first type and the second type may be present in a ratio between about 12:1 and about 3:1.

The types of absorbent articles may differ from one another in more aspects than just the absorbent structure and appearance. For example, one type of absorbent article may include an enhanced liner compared to another type of absorbent article. Each type of absorbent article within the package may be designed to fit wearers of the same size. Additionally, each absorbent article within the package may be designed to fit wearers during a single stage of development. Furthermore, each absorbent article within the package may be a complete absorbent article, rather than being provided as separate components that may be combined to form a complete absorbent article.

A method of providing a package of disposable absorbent articles may be carried out by producing at least two different types of disposable absorbent articles each having an absorbent structure that differs from the absorbent structure present in the other types of absorbent articles. The different types of absorbent articles have an appearance that is visibly distinguished from one another. The different types of absorbent articles are packaged in a single package prior to distribution to consumers.

The various types of absorbent articles may be formed on a single product line. For example, a conventional absorbent structure forming method can be modified using a forming screen having various pocket depths along a length of the screen to form absorbent structures that differ from one another. More particularly, every third, fourth, sixth, or twelfth pocket, for example, can have a higher depth than normal to produce a higher absorbency article through zoning. Alternatively or additionally, a forming drum having variably-shaped contour rings can be used to form absorbent structures that differ from one another in shape and/or dimensions.

As yet another alternative for enhancing the absorbent features in some or all of the articles, an absorbent pledget can be added to a flat or zoned primary absorbent layer. The pledget can be added in just a portion of the absorbent layer or across the entire absorbent layer, and may contain a special superabsorbent and/or fibrous material. The pledget may be formed online or brought to the converting line on a roll to be cut and placed as desired.

A printing-based registering system can be used to create the visual distinction between the different types of absorbent articles. For example, a wax-jet printing-based registering system can imprint a graphical representation on one type of article that designates that type of article as suitable for overnight use. Any suitable process control method can be used, such as a closed-loop feedback system that identifies an absorbent article having a different absorbent structure, surge, or liner than a preceding absorbent article as a precursor signal to activate a registering system to create the visual distinction on the absorbent article having the different absorbent structure. The feedback system may identify such differences between absorbent articles as weight, basis weight (grams per square meter, GSM), and/or dimension of the absorbent structure. For instance, high-speed microwave or laser-based GSM/weight measuring devices can be placed upstream to trigger the downstream registering system.

By providing a single package that contains at least two different types of absorbent articles that are visually distinguished from one another, consumers can purchase a single package of absorbent articles that can accommodate a wearer during at least two different levels of usage, and can quickly identify which absorbent article in the package is most appropriate for a particular severity of expected usage, such as less-severe daytime use or more-severe overnight use.

This combination packaging results in significant cost savings through the use of less absorbent material and/or less expensive absorbent material in at least one of the types of absorbent articles. Additionally, the message of "enhanced care" is conveyed to consumers through the personalization of multiple types of absorbent articles within a single package, as well as the convenience of not having to buy separate overnight or higher absorbency type products.

With the foregoing in mind, it is a feature and advantage of the invention to provide a package of absorbent articles that can provide suitable articles for various usage conditions without requiring excess storage space. It is another feature and advantage to provide a method of making absorbent articles that can produce multiple types of absorbent articles simultaneously on a single product line.

BRIEF DESCRIPTION OF THE DRAWINGS

These and other objects and features of this invention will be better understood from the following detailed description taken in conjunction with the drawings, wherein.

DEFINITIONS

Within the context of this specification, each term or phrase below will include the following meaning or meanings.

"Absorbent article" includes personal care absorbent articles such as diapers, diaper pants, training pants, swimwear, absorbent underpants, adult incontinence products, feminine hygiene products, and the like, as well as medical absorbent articles such as medical absorbent garments, bandages, masks, wound dressings, underpads, wipes, and the like. The term "disposable absorbent article" refers to absorbent articles that are typically disposed of after 1-5 uses.

Figure 4:
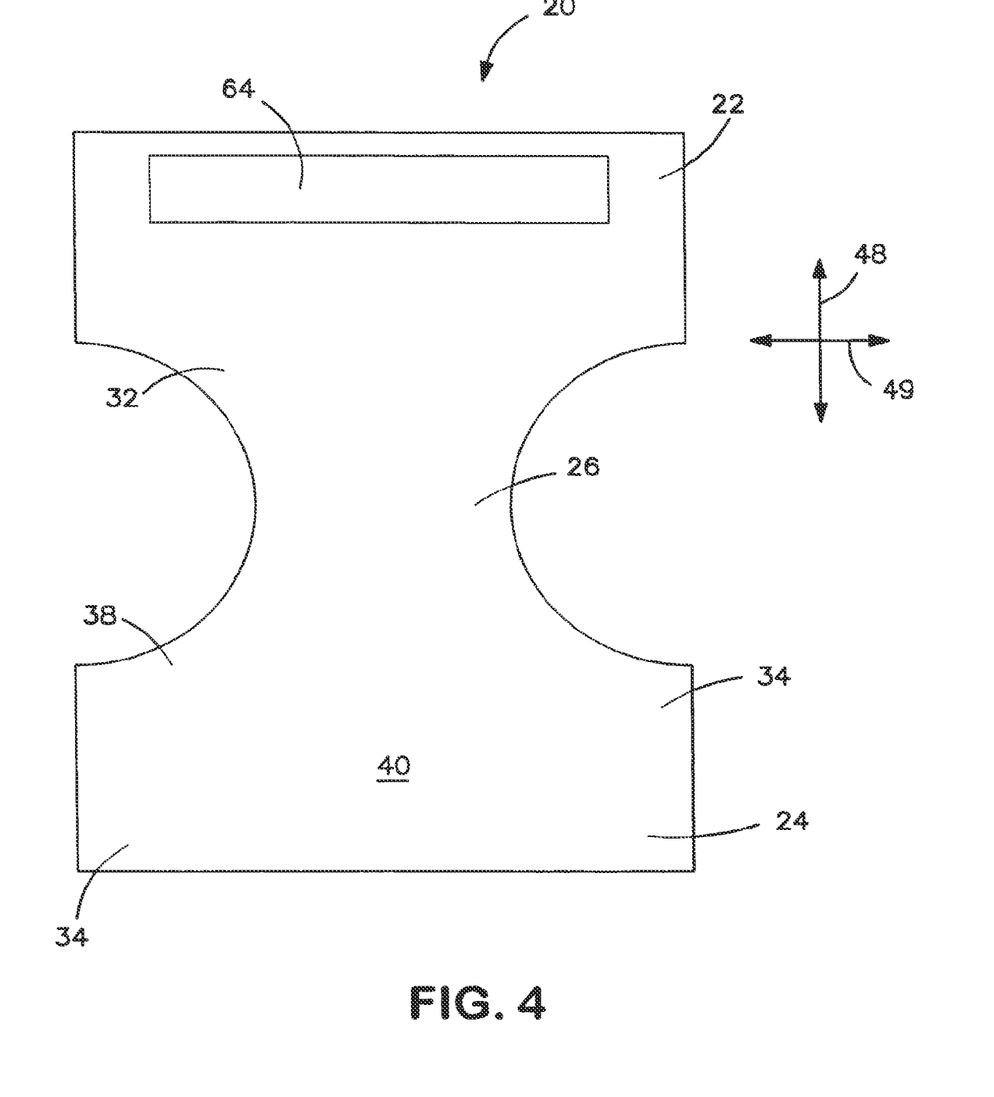
FIG. 4 is a plan view of an absorbent article similar to the absorbent article of FIG. 3 in a stretched flat state, and showing the surface of the article that faces away from the wearer when the article is worn.
Figure 5:
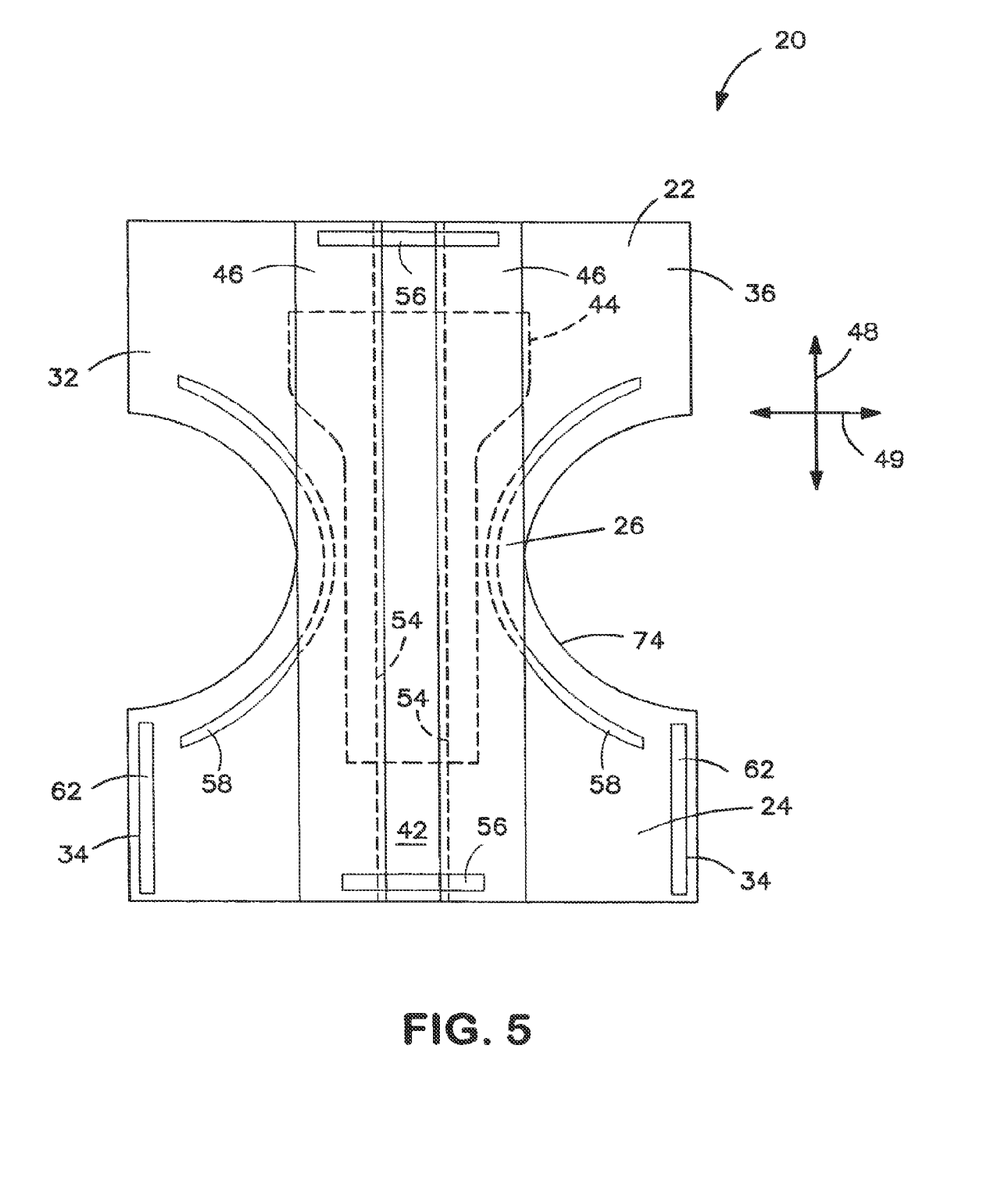
FIG. 5 is a plan view of an absorbent article similar to the absorbent article of FIG. 3 in a stretched flat state, and showing the surface of the article that faces the wearer when the article is worn.
Figure 6:
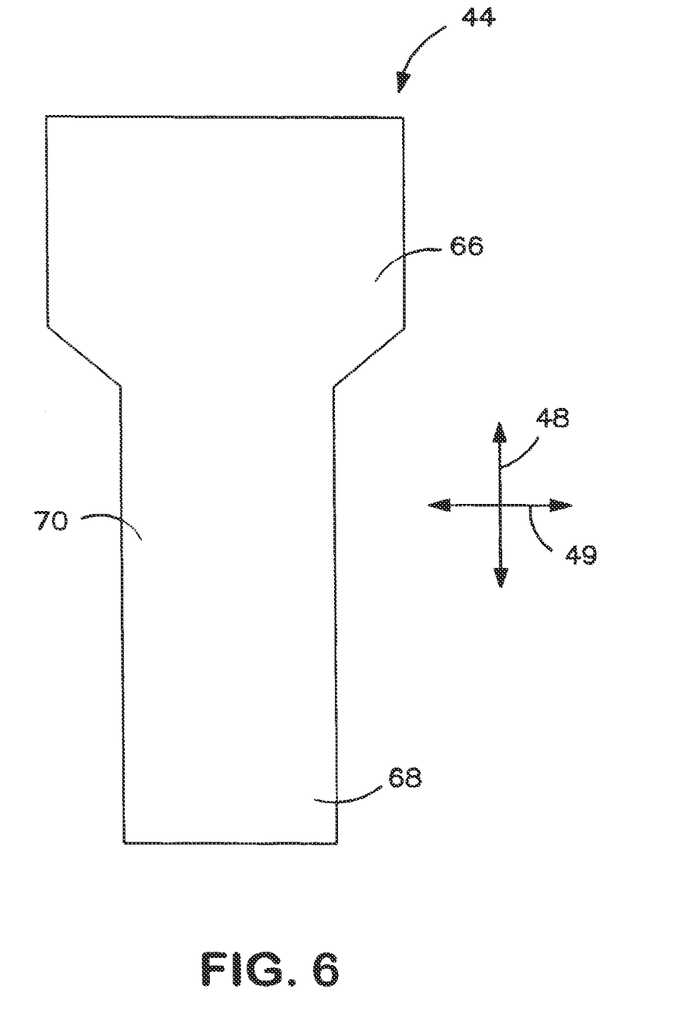
FIG. 6 is a plan view of an absorbent structure.

"Longitudinal" and "transverse" have their customary meaning, as indicated by the longitudinal and transverse axes depicted in FIGS. 4-6. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Superabsorbent" refers to a water-swellable, water-insoluble organic or inorganic material capable, under the most favorable conditions, of absorbing at least about 15 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. The superabsorbent material may be biodegradable or non-biodegradable. The superabsorbent materials can include particles, fibers, tows, flakes, films, foams, and the like. A material is "absorbent" if it absorbs at least five times its weight of the aqueous solution under these conditions.

These terms may be defined with additional language in the remaining portions of the specification.

DESCRIPTION OF PREFERRED EMBODIMENTS

In accordance with the invention, multiple types of disposable absorbent articles are contained within a single package. The various types of absorbent articles are suitable for various usage conditions.

The principles of the present invention can be applied to any suitable disposable absorbent article. Examples of such suitable absorbent articles include diapers, diaper pants, training pants, swimwear, absorbent underpants, adult incontinence products, feminine hygiene products, and the like, as well as medical absorbent articles. For ease of explanation, the description hereafter will be in terms of a diaper.

Figure 1:
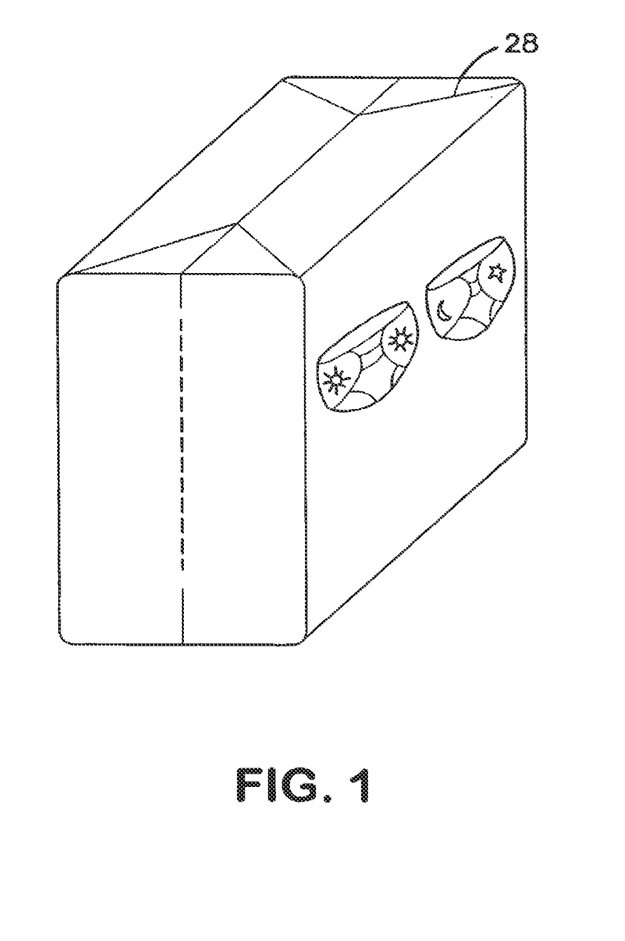
FIG. 1 is a perspective view of a package of absorbent articles.
Figure 2A:
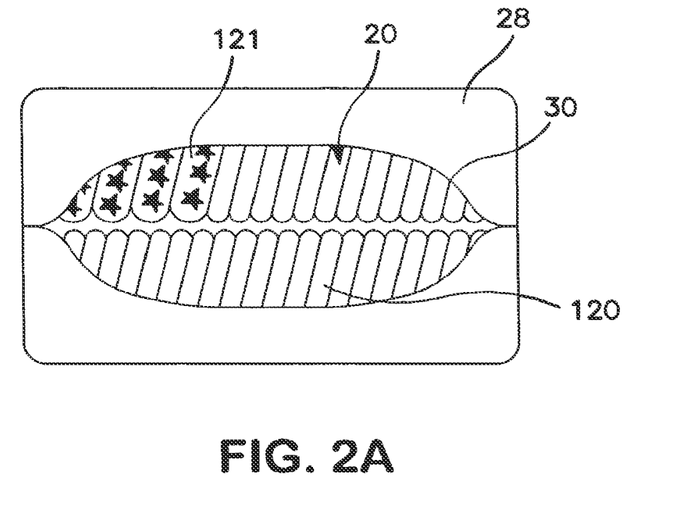
FIGS. 2A and 2B are front views of different embodiments of the package of FIG. 1 in an opened position.
Figure 2B:
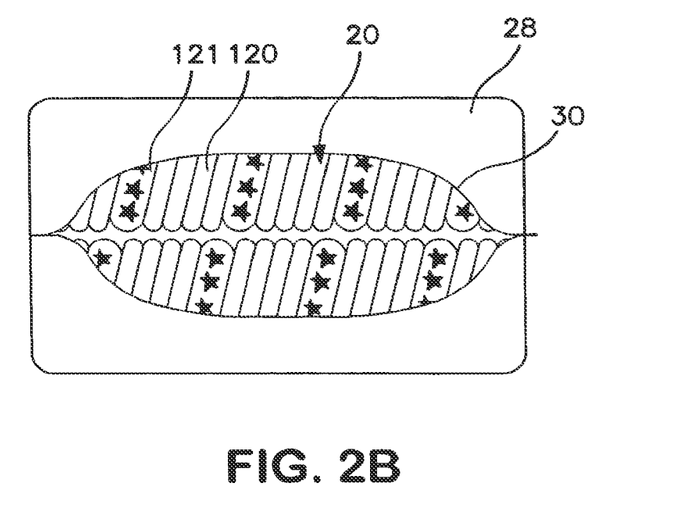

Referring to FIG. 1, a sealed package 28 containing multiple types of diapers is illustrated. FIGS. 2A and 2B illustrate the package 28 with an opening 30 along one surface, thereby displaying the diapers 20 within the package 28. As shown in FIGS. 2A and 2B, a first type 120 of diaper is visually distinguished from a second type 121 of diaper, which enables a consumer to easily identify a most appropriate type of diaper without having to dig through the package 28 or maintain multiple packages. The different types of diapers 20 may be grouped collectively, with all of the first type 120 grouped together and all of the second type 121 grouped together, as shown in FIG. 2A, or the different types of diapers 20 may be interspersed in a discrete repeated order, as shown in FIG. 2B. The various types of diapers 20 have absorbent characteristics that differ from one other. For example, the first type 120 of diaper may have a lower absorbent capacity and hence may be more appropriate for daytime usage, whereas the second type 121 of diaper may have a greater absorbent capacity and may be more appropriate for nighttime usage. Absorbent capacity may be determined according to the test method described in detail below.

The various types of diapers 20 may be visually distinguished from one another in any suitable manner that renders the diapers' appearances easily distinguishable from one another. For example, different types of diapers 20 may have different forms of indicia such as character, symbols, or object graphics printed thereon, or one type of diaper may have no graphics at all. Alternatively, the different types of diapers 20 may be either wholly or partially different colors than one another or have different text identifying the absorbency characteristics included thereon. In certain embodiments, the indicia may be intuitive such that the article's intended use is easily or immediately understood by the user or caregiver. In other embodiments, the indicia may be nonintuitive such that a more detailed explanation may be required to convey the article's intended use to the user or caregiver. Thus, instructions explaining the applicability of each type of article in specific use conditions may be included in or on the package 28, and/or on the diapers 20 themselves.

The frequency of the different types of absorbent articles 20 within a single package 28 may be any suitable frequency. For example, in a package 28 containing at least two different types of absorbent articles, the first type 120 and the second type 121 may be present in a ratio between about 12:1 and about 3:1. Suitably, there is more than one of each type of absorbent article in a single package 28.

Figure 3:
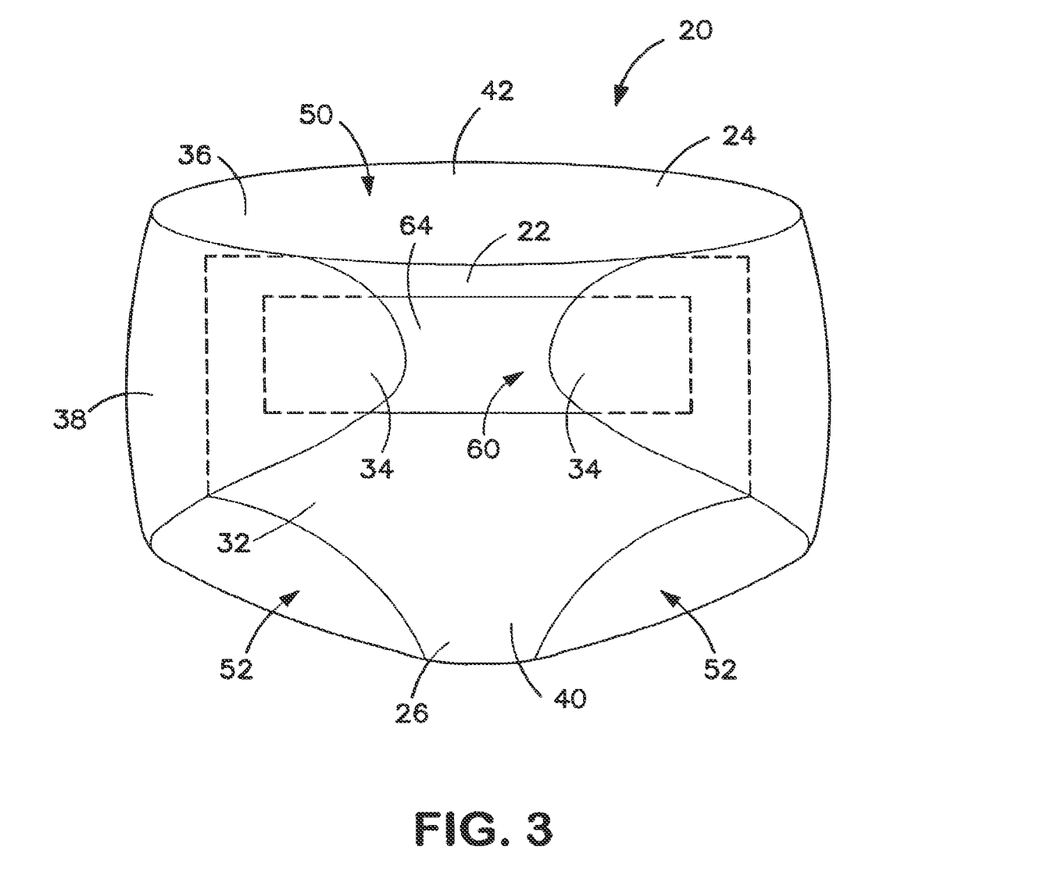
FIG. 3 is a perspective view of an absorbent article, such as a diaper, in a fastened position.

One example of a diaper 20 that may be included in the package 28 is illustrated in FIG. 3 in a fastened position as the garment would appear when worn. FIGS. 4 and 5 illustrate the diaper 20 in a stretched flat state in which the various dimensions of the garment are measured. More particularly, FIG. 4 is a view of a garment-facing outer surface 38 of the diaper 20, and FIG. 5 is a view of a body-facing inner surface 36 of the diaper 20. The diaper 20 includes an absorbent chassis 32 defining a front waist region 22, a back waist region 24, and a crotch region 26 interconnecting the front and back waist regions. In the fastened position, the absorbent chassis 32 defines a three-dimensional pant configuration having a waist opening 50 and a pair of leg openings 52. The chassis 32 includes a body side liner 42 which is configured to contact the wearer, and an outer cover 40 opposite the body side liner which is configured to contact the wearer's clothing. An absorbent structure 44 (FIG. 5) is positioned or located between the outer cover 40 and the body side liner 42. The absorbent structure 44 has a shorter length and width than the outer cover 40 and body side liner 42 and is spaced inboard from all edges of the outer cover 40 and body side liner 42.

The absorbent structure 44 suitably differs among each type of diaper 20 within the package, which creates different absorbent characteristics among the types of diapers. The differences may result in different absorbent capacities, or the absorbent capacities may be the same in each type of diaper while the diapers possess different absorbent performance characteristics. An example of the absorbent structure 44 is illustrated in FIG. 6.

The absorbent structure 44 can be any structure which is generally compressible, conformable, non-irritating to the wearer's skin, and capable of absorbing and retaining liquids and certain body wastes at anticipated levels despite the narrowed crotch width. The absorbent structure 44 can be manufactured in a wide variety of sizes and shapes, and from a wide variety of liquid absorbent materials commonly used in the art. For example, the absorbent structure 44 can suitably include a matrix of hydrophilic fibers, such as a web of cellulosic fluff, mixed with particles of a high-absorbency material commonly known as superabsorbent material. In certain embodiments, the absorbent structure 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 44 to better contain and absorb body exudates. The absorbent structure 44 can have variable thickness, with greater thickness in "target" areas, such as in a central portion of the crotch region. The concentration of the superabsorbent particles can also vary through the thickness of the absorbent structure 44. Alternatively, the absorbent structure 44 can include a laminate of fibrous webs and superabsorbent material or other suitable means of maintaining a superabsorbent material in a localized area. The absorbent structure 44 may or may not be wrapped or encompassed by a suitable tissue wrap that maintains the integrity and/or shape of the absorbent structure 44.

In certain embodiments, the absorbent structure 44 may differ in geometry. These differences may be achieved through the design of contour rings on a forming drum, as described in greater detail below. A front region 66 of the absorbent structure 44 includes the portion of the absorbent structure 44 which, when the diaper 20 is worn, is positioned on the front of the wearer while a back region 68 includes the portion of the absorbent structure 44 which, when the diaper 20 is worn, is positioned on the back of the wearer. A crotch region 70 of the absorbent structure 44 includes the portion of the absorbent structure 44 which, when the diaper 20 is worn, is positioned between the legs of the wearer and covers the lower torso of the wearer. A longitudinal length of the absorbent structure 44 is the distance between (and including) the front region 66 and the back region 68. For reference, arrows 48 and 49 depicting the orientation of the longitudinal axis and the transverse axis, respectively, of the diaper 20 and the absorbent structure 44 are illustrated in FIGS. 4-6.

For instance, a width of the crotch region 70 of each absorbent structure 44 may differ from one diaper type to another.

A narrow crotch width provides better crotch fit, reduced bulkiness, and improved comfort and mobility. Thus, a narrow crotch width is suitable when a diaper is applied for short-term use, or when the type of diaper is intended to be changed frequently, such as during daytime wear. A wider crotch width is suitable for reducing the risk of leakage, such as during times when a diaper change would be difficult to maneuver, as during traveling, or when it is anticipated that the diaper will be worn for an extended period of time, such as overnight.

As another example of differing geometry, each type of diaper may differ in width in the front region 66 of the absorbent structure 44. A narrow, body-contoured shaping in the front region 66 of the absorbent structure 44 provides optimum fit and appearance in the front of the diaper when the wearer is awake and active. A widened front region of the absorbent structure 44 creates storage space for directing an increased absorbent level to the front region to provide enhanced leakage performance, such as when the wearer is in a prone position during naps and nighttime use.

The types of diapers may also differ in width in the back region 68 of the absorbent structure 44. Narrow, body-contoured shaping in the back region 68 of the absorbent structure 44 provides optimum fit and appearance in the back of the diaper when the wearer is awake and active. A widened back region of the absorbent structure 44 creates storage space for directing an increased absorbent level to the back region to provide enhanced urine and feces containment, such as when the wearer is in a reclined (for example, in a car seat) or supine position.

The absorbent structure 44 may also vary in length among the different types of diapers. A standard length absorbent structure 44 is suitable for general-use situations. A shortened length absorbent structure 44 may maintain the same absorbent mass as a standard length pad for specific use conditions, such as activity-dependent or position-dependent conditions. For example, the absorbent structure 44 may be shortened in the back region 68 to direct more absorbency to the front region 66, or shortened in the front region 66 to direct more absorbency to the back region 68, or shortened in both the front region 66 and the back region 68 to direct more absorbency to the center crotch region 70.

Alternatively or additionally, the absorbent structure 44 may be zoned differently among the different types of diapers, with either no zoning (namely, a uniform web) present in one type and/or different zoning in front/back or front/crotch/back regions among the diaper types. These zone design differences may be achieved through forming screen design and scarfing control, as described in greater detail below. For instance, a uniform zone shape that provides a balance of performance and fit attributes for universal use situations provides neither optimum performance nor optimum fit for any situation, but may be adequate for a wide range of use conditions. In contrast, absorbent structures 44 having a specially zoned width, length, and/or shape can be leveraged to provide specific performance or fit benefits based on user position or activity. Examples include predominantly front region 66 zoning for better leakage performance for prone sleeping male babies or body-contoured topographic zone shapes for better fit.

More particularly, one type of diaper 20 may have an absorbent structure 44 that is zoned to provide a balance of performance and fit attributes for universal use, such as a front/back or back/front ratio of 1:1 for a flat pad or 1.5:1 for a lightly zoned pad when appearance is more important than leakage risk. Another type of diaper 20 may have an absorbent structure 44 that is zoned in a location that provides optimum performance while the wearer is in specific positions or engaging in specific activities, such as a front/back or back/front ratio of 3:1 for a moderately zoned pad or greater than 3:1 for a highly zoned pad when fit is less important to the consumer or it is anticipated that the diaper will be worn for an extended period of time. For example, a zoned area may be located in the back region 68 of the absorbent structure 44 for a type of diaper used during periods when the wearer is in a reclined (such as in a car seat) or supine position.

The absorbent structure 44 may be bonded or embossed differently among the diaper types, and/or not bonded or embossed at all in one of the diaper types. The bonding or embossing may be achieved on-line using timed bonding, embossing, or printing technologies, as known to those skilled in the art. Special bonding or embossing patterns may be applied to the absorbent chassis or the absorbent structure 44 or one or more types of diapers to provide unique functional, fit, or perceptual benefits or cues, such as a wetness indicator.

The absorbent structure 44 may vary in density among the different types of diapers 20. For example, the absorbent capacity may be consistent among the absorbent structures 44 in the different diaper types, while the density of the absorbent structure 44 in one diaper type is greater than the density of the absorbent structure 44 in another diaper type. Additionally or alternatively, the absorbent structures 44 may have variable density in different regions of the absorbent structures 44 among the different types of diapers. For example, one type of diaper may have a greater density in the crotch region 70 of the absorbent structure 44 compared to the absorbent structure 44 in another type of diaper.

In certain embodiments, different types of superabsorbent material may be used among the different types of diapers 20. The delivery of different superabsorbent materials may be achieved using a pulsed superabsorbent delivery system. For example, the absorbent structure 44 in one type of diaper 20 may include a superabsorbent material that provides adequate performance for many general-use situations but fails to deliver optimum performance under some use conditions. Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., BASF located in Portsmouth, Va., U.S.A., and Degussa in Greensboro, N.C., U.S.A. Typically, a superabsorbent material is capable of absorbing at least about 15 times its weight in water, and desirably is capable of absorbing more than about 25 times its weight in water.

Another type of diaper 20 may include a special type of superabsorbent material that is used in diapers designed to provide unique benefits not provided by the standard superabsorbent material. The special superabsorbent may provide superior composite permeability, void volume, and/or intake even at high saturation levels to enhance leakage performance for extended wear conditions. Alternatively, the special superabsorbent may provide faster absorbency rate and/or improved dryness compared to the normal superabsorbent. As another alternative, the special superabsorbent may have better feces dewatering and containment properties than the normal superabsorbent. The high cost and limited availability of these special superabsorbents limits their use to only a relatively small proportion of diapers. Examples of special superabsorbents are described, for example, in U.S. Pat. No. 6,222,091 issued 24 Apr. 2001 to Beihoffer et al., U.S. Pat.

No. 5,149,335 issued 22 Sep. 1992 to Kellenberger et al., U.S. Pat. No. 6,689,934 issued 10 Feb. 2004 to Dodge II et al., U.S. Patent Publication 2003/0139715 published 24 Jul. 2003 by Dodge, II et al., U.S. patent application Ser. No. 10/631,916 filed 31 Jul. 2003 by Qin et al., and U.S. patent application Ser. No. 10/655,940 filed 5 Sep. 2003 by Qin et al., each of which is incorporated herein by reference in its entirety in a manner consistent with the present document.

As yet another example of possible differentiating features among the types of diapers 20, a specific type of surge layer may be present in the absorbent structure 44 of one type and the absorbent structure 44 of another type may have either no surge layer or a different type of surge layer. The surge layer (if present) may be achieved using a cut-and-place on-line process, as known to those skilled in the art. A standard surge layer present in the absorbent structure 44 of one type of diaper may provide adequate performance for many general-use situations, but fails to deliver optimum performance in certain usage situations. Therefore, a surge layer present in the absorbent structure 44 of another type of diaper may possess special surge material or may be designed to provide unique urine leakage prevention, feces containment, and/or skin dryness benefits not delivered by the standard surge design. Features that may be included in this special surge layer include surge type, length, width, weight, placement, fluid handling properties, apertures, and topography.

In certain embodiments, an absorbent pledget can be added to a flat or zoned absorbent structure 44. The pledget can be added in just a portion of the absorbent structure 44 or across the entire absorbent structure 44, and may contain a special superabsorbent and/or fibrous material. Although not necessary, the pledget could maintain an equal overall absorbent capacity in the absorbent structure 44, if desired. The pledget may be formed online or brought to the converting line on a roll to be cut and placed as desired.

The outer cover 40 of the diapers 20 suitably includes a material that may be substantially liquid impermeable or liquid permeable, and can be elastic, stretchable, extensible, non-stretchable, or non-extensible. The outer cover 40 can be a single layer of liquid impermeable material, but suitably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer of the outer cover 40 desirably includes a material that can be elastic, stretchable, extensible, non-stretchable, or non-extensible. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.02 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Certain "non-breathable" elastic films can also be used to make the outer cover 40. Examples of suitable non-breathable films can be made of styrene-ethylene-butylene-styrene or styrene-isoprene-styrene block copolymers, KRATON® polymers from Kraton Inc. of Houston, Tex., U.S.A., metallocene catalyzed elastomers or plastomers, and the like. Other materials suitable for making the outer cover 40 include monolithic breathable films, such as those made of polyether amide based polymers, for example PEBAX, and ether/ester polyurethane thermal-plastic elastomers.

The liquid permeable body side liner 42 is illustrated as overlying the outer cover 40 and absorbent structure 44, and may but need not have the same dimensions as the outer cover 40. The body side liner 42 is desirably compliant, soft feeling, and non-irritating to the wearer's skin. Further, the body side liner 42 can be less hydrophilic than the absorbent structure 44, to present a relatively dry surface to the wearer and permit liquid to readily penetrate through its thickness. The body side liner 42 desirably includes a material that can be elastic, stretchable, extensible, non-stretchable, or non-extensible.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 available from Uniqema Inc., a division of ICI of New Castle, Del., U.S.A. and GLUCOPON® 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, or the like. While the outer cover 40 and body side liner 42 can include extendible and/or elastomeric materials, it can be desirable in some embodiments for the composite structure to be generally inelastic, where the outer cover, the body side liner and the absorbent structure include materials that are generally not elastomeric.

The types of diapers 20 may differ from one another in more aspects than just the absorbent structure 44 and appearance. For example, one type of diaper 20 may include an enhanced body side liner 42 compared to another type of diaper 20. The enhancement of the body side liner 42 may be achieved on-line through the addition of additives, or by conducting a mechanical operation on the selected type(s). A standard body side liner 42, such as described above, may be used in one or more diaper types and may deliver adequate performance for many general-use situations, but does not deliver the required performance for some usage conditions. Another diaper type may include a special body side liner 42 execution that provides unique urine leakage prevention, feces containment, skin health, and/or aesthetic benefits that are not delivered by the standard liner design. Potential attributes of this enhanced body side liner 42 include higher fluid wettability treatment level, special treatment to reduce fluid rewet, higher fluid or feces permeability through apertures or other surface topography, ointment type/amount, and/or fragrance type/amount.

In certain embodiments, the types of diapers 20 may differ from one another only in terms of the absorbent structure 44 and appearance. More particularly, the chassis 32 may have the same overall dimensions, or the same footprint, among each of the different types of diapers 20. The "footprint" refers to the overall length and width dimensions (not the depth dimension) of a garment when in a laid flat configuration. Furthermore, each of the different types of diapers 20 may have outer covers 40 and/or body side liners 42 of the same dimensions and the same materials as one another, although the different types of diapers 20 may have different graphics or other indicia on the outer covers 40 or other parts of the diapers in order to distinguish the different types of diapers from one another.

The absorbent chassis 32 may further include a pair of transversely opposed ear panels or tabs 34, which extend transversely outward along the back waist region 24 of the absorbent chassis 32. The tabs 34 may be integrally formed with the outer cover 40 and/or the body side liner 42, as shown in FIGS. 4 and 5, or may include two or more separate elements.

The diaper 20 may also include a waist elastic member 56 in the front waist region 22, in the back waist region 24, or in both the front and back waist regions 22, 24 of the garment, operatively attached to the outer cover 40 and/or body side liner 42 and extending across part or a full length of the waist regions.

To further enhance containment and/or absorption of body exudates, the diaper 20 may also include leg elastic members 58, as are known to those skilled in the art. The leg elastic members 58 may be operatively joined to the outer cover 40 and/or body side liner 42 along opposite side edges of the absorbent chassis 32 and positioned in the crotch region 26 of the diaper 20.

The waist elastic members 56 and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 56 may include a polystyrene-polyethylene-polypropylene-polystyrene (SEPS) block copolymer, such as KRATON® G2760, available from Kraton Inc. of Houston, Tex., U.S.A.

The diaper 20 may be refastenable, thereby including a refastenable fastening system 60 (FIG. 3) for securing the diaper about the waist of the wearer. One example of a suitable refastenable fastening system 60 may include fastening components 62, such as hook components, located along or adjacent to distal edges of the tabs 34. Suitable single-sided hook materials are available from Velcro Industries B.V., Amsterdam, Netherlands, or affiliates thereof. The fastening components 62 are adapted to refastenably connect to mating fastening components 64, such as loop material, located on an outer surface of the front waist region 22. One example of suitable loop material is "point unbonded" material. Point unbonded materials are fabrics having continuous thermally bonded areas defining a plurality of discrete unbonded areas and are described in greater detail in U.S. Pat. No. 5,858,515 issued Jan. 12, 1999 to Stokes, et al., incorporated herein by reference. The engaging elements of the fastening components 62 are adapted to repeatedly engage and disengage the engaging elements of the mating fastening components 64.

To enhance containment and/or absorption of any body exudates discharged from the wearer, the chassis 32 may include a pair of containment flaps 46 which are configured to provide a barrier to the transverse flow of body exudates. A flap elastic member 54 (FIG. 5) may be operatively joined with each containment flap 46 in any suitable manner as is well known in the art. The elasticized containment flaps 46 define an unattached edge which assumes an upright, generally perpendicular configuration in at least the crotch region 26 of the diaper 20 to form a seal against the wearer's body. The containment flaps 46 can be located along the transversely opposed side edges of the chassis 32, or in the crotch region 26, and can extend longitudinally along the entire length of the chassis or may only extend partially along the length of the chassis. Suitable constructions and arrangements for the containment flaps 46 are generally well known to those skilled in the art.

As described herein, the various components of the diaper 20 can be integrally assembled together employing various types of suitable attachment means, such as adhesive, sonic and thermal bonds or combinations thereof.

Each type of absorbent article 20 within the package 28 may be designed to fit wearers of the same size, such that each article within the package is designed to fit the same wearer during a single stage of development, as opposed to being designed for wear during different stages of development, for example a crawling stage versus a walking stage. Additionally, each absorbent article 20 within the package 28 may be a complete absorbent article, rather than being provided as separate components that may be combined to form a complete absorbent article. More particularly, the absorbent structure 44 is contained in its entirety within each absorbent article 20, and any separate absorbent structure 44 or absorbent structure component is not considered to be a complete absorbent article.

The invention also includes a method of providing a package 28 of disposable absorbent articles 20. The method includes producing at least two different types of disposable absorbent articles, each having an absorbent structure that differs from the absorbent structures in the other types of absorbent articles. Each type of absorbent article is also visibly distinguishable from one another in appearance. The different types of articles are packaged together in a single package.

Figure 7:
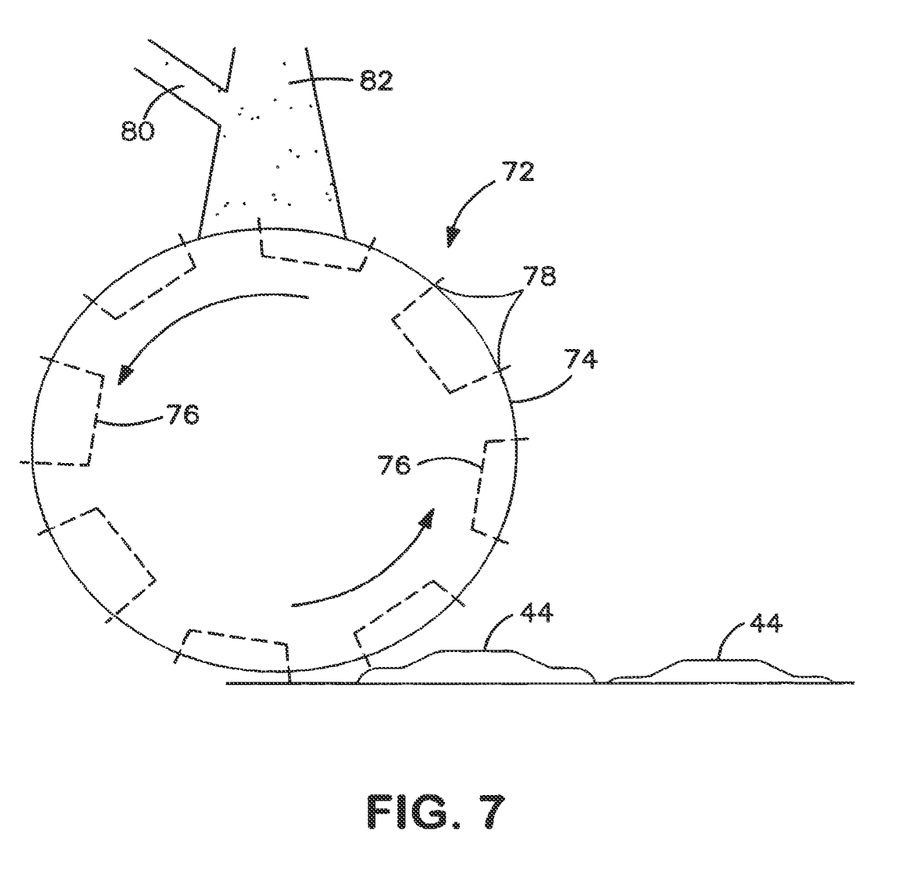
FIG. 7 is a plan view of a drum former used to form different types of absorbent articles.

The different types of disposable absorbent articles 20 can be formed on a single product line. More particularly, a conventional absorbent structure-forming method can be modified to produce the different types of articles on the same line. A suitable forming drum 72 for the product line is illustrated in FIG. 7.

A forming screen 74 on the forming drum 72 may have various pocket depths 76 along a length of the screen 74 to form absorbent structures 44 having a variety of zone designs. For example, every third, fourth, sixth, or twelfth pocket 76, for example, in the forming screen 74 can have a higher depth than a conventional absorbent structure to produce a higher absorbency diaper through zoning. Additionally, in certain embodiments, the absorbent structures formed in deeper pockets may have a greater density than the absorbent structures formed in shallower pockets.

The forming drum 72 may have variably-shaped contour rings 78 on the forming screen 74 to form absorbent structures 44 having geometrical shapes that differ from one another. These contour rings 78 may be used to configure the crotch region width, front region width, back region width, and longitudinal length of the absorbent structures 44.

As mentioned above, a pulsed superabsorbent delivery system can be used to vary the type and/or amount of superabsorbent material 80 among the different types of absorbent articles 20. More particularly, the superabsorbent material 80 may be fed into a fluff stream 82 prior to reaching the forming drum 72.

Figure 8:
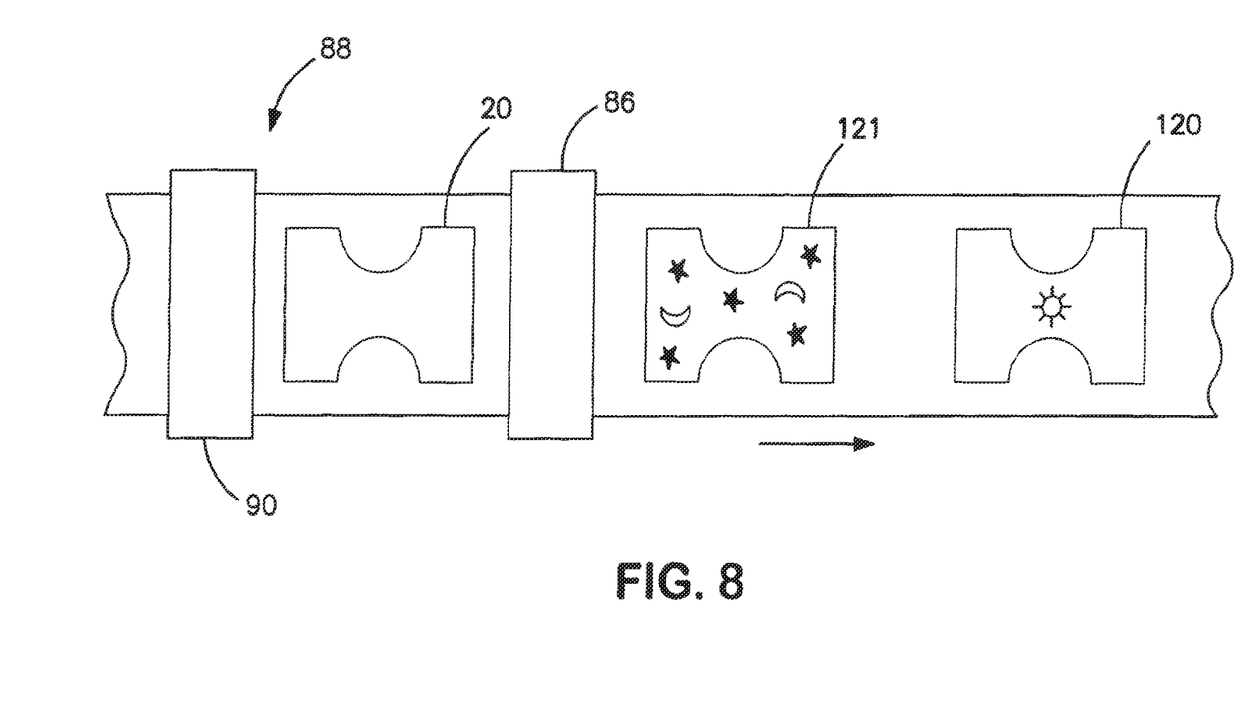
FIG. 8 is a plan view of a registering system along a product line.

FIG. 8 illustrates a printing-based registering system 86, such as a wax-jet printing-based registering system, along the product line for creating the visual distinction between the different types of absorbent articles. A closed-loop feedback system 88 can be used to identify an absorbent article having a different absorbent structure than a preceding absorbent article. The feedback system 88 may detect the different types of absorbent articles based on the weight, basis weight (grams per square meter or GSM), and/or dimension of the diaper or absorbent structure. For example, a high-speed microwave or laser-based GSM or weight-measuring device 90 may be placed upstream to trigger the downstream registering. Once a different type of absorbent article is identified, the feedback system 88 generates a precursor signal that activates the registering system 86 to create the visual distinction on the different type of absorbent article.

The absorbent articles may be packaged in any suitable unitary packaging constructed of any suitable packaging material, such as paper or a polymer. Suitably, the package may be constructed of a flexible polymer film having sufficient strength to hold and contain the absorbent articles without breaking and without excessive bulging or stretching of the film material. For example, the film material may be composed of a polyethylene film or film laminate having a thickness of about 2.0 mils (about 0.0508 millimeters). Furthermore, the film may include a LDPE (low density polyethylene) film, a LDPE/LLDPE (linear low density polyethylene) film laminate, a LDPE/MDPE (medium density polyethylene) film laminate, a LDPE/HDPE (high density polyethylene) film laminate or the like. The package, or at least portions thereof, can be transparent to enable a consumer to view the different types of absorbent articles within the package prior to purchasing the package.

The different types of absorbent articles within a single package can be produced at a cost savings due to the reduced cost of absorbent materials used in the articles intended for milder usage conditions. This combination of absorbent article types in the same package also provides consumers with the convenience of at least two different types of garments suitable for different usage conditions without having to purchase or store more than one package at a time.

Test Methods

Saturated Retention Capacity of Absorbent Articles

The saturated retention capacity is a measure of the total absorbent capacity of the absorbent article. The saturated retention capacity is determined as follows. The absorbent garment to be tested, having a moisture content of less than about 7 weight percent, is weighed and then submerged in an excess quantity of room temperature (about 23 degrees Celsius) saline solution, described below. The garment is allowed to remain submerged for 20 minutes. After 20 minutes, the absorbent garment is removed from the saline solution and placed on a TEFLON® coated fiberglass screen having 0.25-inch openings (commercially available from Taconic Plastic Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The absorbent garment is weighed again. The amount of aqueous liquid retained by the absorbent garment is determined by subtracting the dry weight of the absorbent garment from the wet weight of the absorbent garment (after application of the vacuum) and is reported as the saturated retention capacity in grams of aqueous liquid retained.

The saline solution is an aqueous solution of about 0.9 percent sodium chloride by weight. A suitable product is S/P® certified blood saline, commercially available from Baxter Diagnostics in Deerfield, Ill.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of producing and packaging disposable absorbent articles, comprising:

producing a first type of disposable absorbent article having an absorbent structure on a product assembly line wherein the absorbent structure is formed by a forming apparatus;

producing a second type of disposable absorbent article having an absorbent structure on the same product assembly line as the first type of disposable absorbent article wherein the absorbent structure in the second type of disposable absorbent article is formed by the same forming apparatus as the absorbent structure in the first type of disposable absorbent article, the absorbent structure in the second type of disposable absorbent article being different than the absorbent structure in the first type of absorbent article, the second type of disposable absorbent article having an appearance that is visibly distinguished from the first type of absorbent article; and packaging the first type of disposable absorbent article and the second type of disposable absorbent article in a single package.

2. The method of claim 1, wherein the second type of absorbent article has a greater absorbent capacity than the first type of absorbent article.

3. The method of claim 1, wherein the absorbent structure in the first type of absorbent article has a crotch region width that is narrower than a crotch region width of the absorbent structure in the second type of absorbent article.

4. The method of claim 1, wherein the absorbent structure in the first type of absorbent article comprises a first type of superabsorbent material and the absorbent structure in the second type of absorbent article comprises a second type of superabsorbent material.

5. The method of claim 1, wherein the absorbent structure in the second type of absorbent article comprises a type of surge layer that is not present in the absorbent structure in the first type of absorbent article.

6. The method of claim 1, wherein the first type of absorbent articles and the second type of absorbent articles are present in the package in a ratio between about 12:1 and about 3:1.

7. The method of claim 1, comprising rotating a forming drum, the forming drum having a forming screen with a plurality of areas for alternatingly forming the absorbent structures of both the first and second type of disposable absorbent articles on the product assembly line as the forming drum rotates.

* * * * *